June 6, 1961 E. B. LE GRICE Plant Pat. 2,061
HYBRID TEA-ROSE PLANT
Filed March 23, 1960
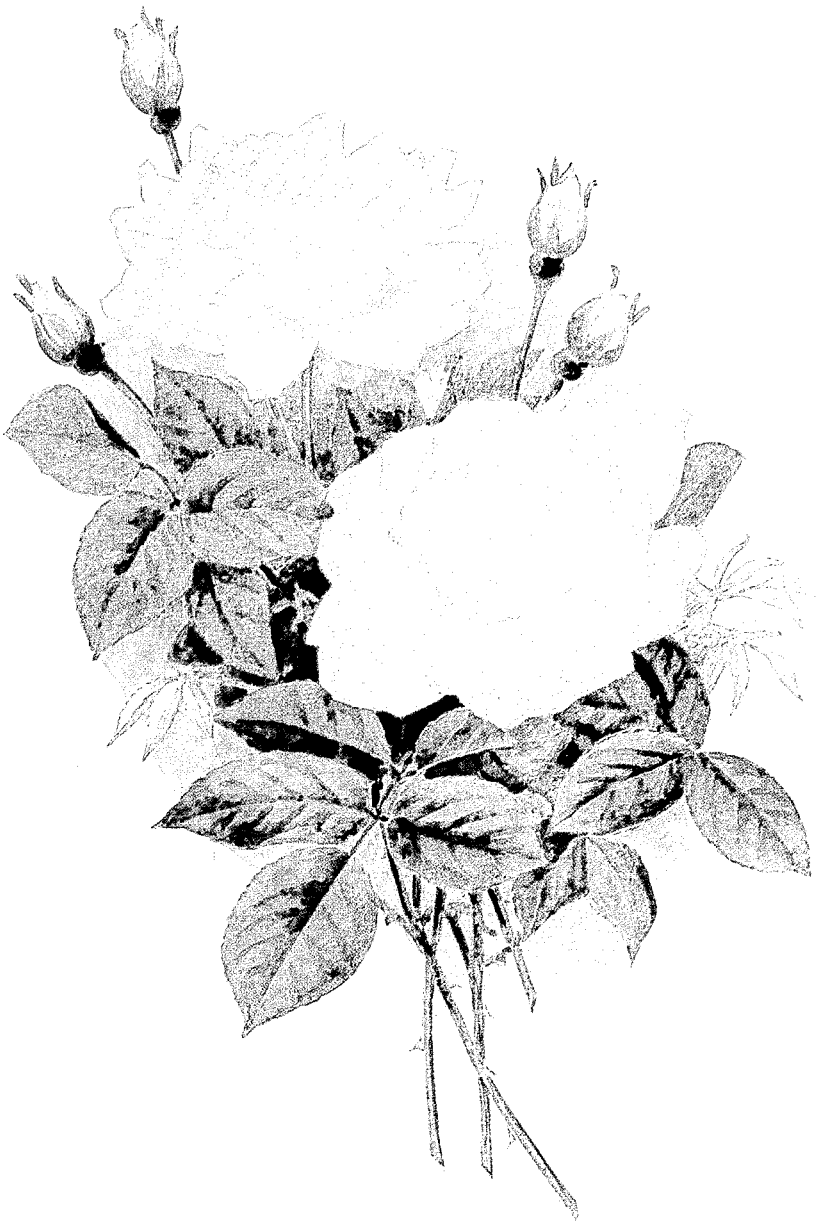
WITNESS
Addison E. Avery
INVENTOR
Edward Burton La Grice,
by:-
John H. Brown Jr.
his ATTY.

United States Patent Office

Plant Pat. 2,061
Patented June 6, 1961

2,061
HYBRID TEA-ROSE PLANT

Edward Burton Le Grice, North Walsham, Norfolk, England

Filed Mar. 23, 1960, Ser. No. 17,237
1 Claim. (Cl. 47—61)

This invention relates to a new variety of hybrid tea-rose plant.

The present rose plant was produced originally by hand crossing under glass an unpatented hybrid tea-rose, known commercially as "Wellworth," as a seed parent, with an unpatented hybrid tea-rose, known commercially as "Ena Harkness," as the pollen parent.

The new variety was asexually reproduced by me, at my nurseries at North Walsham, England, by budding. The new variety has been tested at St. Albans, England; Mentor, Ohio, United States of America; and Boskoop, Holland.

The drawing shows in color typical stalks with leaves, buds, blooms and thorns.

The plant is a woody, compact, bush of upright growth, symmetrical in outline, with a flattened top. It grows to a height of about 2 to 2½ feet in 2 years. It is robust and very hardy.

The exposed portion of the plant has a good resistance to low temperature when protected, and fair resistance when unprotected. Its resistance both to drought and wet seasons is good.

For growth of the bush, it prefers moderate sun and a west and south exposure. It thrives well in rich loam with normal drainage.

The color references herein used are from the British Colour Council and Royal Horticultural Society Colour Charts.

The main stalks of the plant are upright and slightly branched. They grow divergent from the roots. They are relatively stiff and are adequate to support the foliage, blooms, and fruit well.

Both the new growth and the old growth of the stalks is Spinach Green, Sheet 187, No. 0960/1.

The color is relatively uniform on both old and new growth.

The main stalks range from about 9 to 18 inches in length, and grow grouped and upwardly. They have a smooth surface texture with very few thorns. The branches of the main stalks are few in number and are alternately arranged. They are mostly Spinach Green, Sheet 187, No. 0960/1. A few are Indian Lake, Sheet 170, No. 826/3. They have a smooth surface texture with few, if any, thorns, and are relatively stiff and straight.

The foliage in general is open, the leaves being alternately arranged and of medium quantity. The new leaves on the top surface are Spinach Green, Sheet 187, No. 0960/1 with outer edges of Indian Lake, Sheet 170, No. 826/3. On the bottom, the new leaves are Spinach Green, Sheet 187, No. 0960/3 shaded with Indian Lake, Sheet 170, No. 826/3.

The old leaves, on the top and bottom surfaces, are Spinach Green, Sheet 187, No. 0960/1. The coloring is generally uniform.

The leaves are of average size, varying from 3 to 5 inches in length and from 2 to 4 inches in width. They are of the normal shape, being pinnate with serrated margins and with acute apices. They are of average thickness. On the upper face, they are smooth and glossy. On the lower face, they are smooth and dull.

Their persistency on the plant is good.

The petioles or leaf stems are Fern Green, Sheet 186, No. 0862/1 with the midrib Indian Lake, Sheet 170, No. 826/3. They average in length to about 2½ inches and are quite strong. Their surface texture is smooth.

The stipules are Fern Green, Sheet 186, No. 0862/1.

The plant grows and blooms well throughout all temperate regions. It prefers well drained, almost neutral, rich loam soil of pH about 6.5. It prefers sun in a southern or western exposure, and wet and cold seasons.

Better soils produce flowers with more intense color, and increase the quality and quantity of blooms.

The plant blooms recurrently for a period of about five months.

The buds are medium in size and slightly globular in shape. They have a smooth aspect. They are borne upright on terminals. Their color when the sepals first divide is Rose Madder, Sheet 23, No. 23.

When the petals begin to unfurl and also when they are half blown, the color is Rose Madder, Sheet 23, No. 23/1.

The sepals are normal.

The calyx is normal in shape and size, and of smooth surface texture. It is Spinach Green, Sheet 187, No. 0960/1.

The peduncles average from 1 to 2 inches in length. They are smooth and strong. They are spinach green with their bases sometimes shaded with Indian Lake.

The same is true of the pedicels.

The blooms average from 4 to 6 inches in diameter and an average plant will bear about 30 to 35 blooms each season. The blooms are borne singly. On the plant, they last about 5 days, and, when cut, about 5 days. The blooms average about 32 petals each.

The petalage color is various shades of Rose Madder, Sheet 23. The extreme tip of the base of the petals is Aureolin, Sheet 3, No. 3/3. The inside of the petals is Rose Madder. The reverse of the petals is also Rose Madder.

The general tonality of the plant from a distance, when in bloom, is a sparkling Rose Madder. Throughout the blooming period, they become a very slightly lighter Rose Madder, Sheet 23, No. 23 to 23/1.

The petals are thick, smooth, and recurvent. On the inside, they are Rose Madder with Aureolin, Sheet 3, No. 3/3 at the tip of the base. They have the normal arrangement. There are a few petaloids, usually not exceeding three to five. Their persistance, both cut and uncut, is about 5 days. The flowers have the normal shape for hybrid tea-roses of the exhibition type.

The fragrance of the blooms is a very strong damask. The fragrance is very persistent in both cut and uncut flowers.

The stamens are normal and many. In color, they are Saffron Yellow. The filaments are of medium size. They are Rose Madder, Sheet 23 with Saffron Yellow pollen.

The styles are about ¼ of an inch in length and Rose Madder, Sheet 23, in color. The stigmas are about 1/16 of an inch wide, and plentiful. They are Aureolin, Sheet 3, No. 3/3 in color. The ovaries are plentiful.

The fruit is of the usual form and abundance.

The thorns are few on the main stalks and almost absent on the laterals. They are relatively short. In color, they are Rose Madder, Sheet 23, No. 23/1. They are evenly distributed on the main stalk. On the peduncles they are almost absent.

The drawing further illustrates the characteristics of the variety and the following tabulation is a detailed description of the new variety:

*General*

Parentage:

*Seed parent.*—"Wellworth," unpatented, hybrid tea-rose, listed on page 85 of "Roses," 1958, National Rose Society of Great Britain.

*Pollen parent.*—"Ena Harkness," a hybrid tea-rose listed on page 31 of "Roses," 1958, National Rose Society of Great Britain.

Classification: Botanic—hybrid tea.

*Flower*

Blooming habit:

*Location where observations were made.*—Mentor, Ohio, U.S.A., and Boskoop, Holland.

*Flowering.*—Recurrent for about five months from early June until frost.

Bud:

*Size.*—Medium.

*Form.*—Slightly globular, with smooth aspect.

*Color.*—When sepals first divide, when petals begin to unfurl, and when half blown, the color is Rose Madder, Sheet 23, No. 23.

*Sepals.*—Normal.

*Calyx.*—Normal in shape, size, with smooth surface texture.

*Peduncle.*—From one to two inches in length; strong. Color—Spinach Green, Sheet 187. Sometimes shaded with Indian Lake, Sheet 170, No. 826/3.

*Pedicels.*—Average one to two inches in length; strong; smooth. Color—Spinach Green, Sheet 187, also sometimes shaded with Indian Lake, Sheet 170, No. 826/3.

Bloom:

*Size.*—Four to six inches in diameter.

*Borne.*—Singly.

*Stems.*—Length one to two inches; strong; aspect smooth almost free of thorns. Color—Spinach Green, Sheet 187.

*Form.*—When first opened—usual.

*Permanence.*—On the plant, about 5 days; when cut, about 5 days.

Petalage:

*Number of petals under normal conditions.*—Thirty-two.

*Color.*—Rose Madder, Sheet 23. Extreme tip of base, Aureolin, Sheet 3, No. 3/3.

*Variegations.*—The color of each petal is the same throughout from base to tip, except extreme tip of base. Inside is Rose Madder. The reverse is Rose Madder.

*Discoloration.*—Color becomes slightly lighter Rose Madder as blooming season progresses.

Petals:

*Texture.*—Smooth and thick.

*Appearance.*—Rose Madder, Sheet 23.

*Form.*—Recurvent.

*Arrangement.*—Normal.

*Petaloids in center.*—Few, about three to five.

*Persistence.*—Uncut and cut, about five days.

*Fragrance.*—Strong damask.

*Lasting quality.*—Very persistent, uncut or cut.

Genital organs:

*Stamens.*—Normal and many. Color—Staffron Yellow.

*Filaments.*—Medium size. Color—Rose Madder, Sheet 23.

*Pollen.*—Saffron Yellow.

*Styles.*—¼ of an inch long, colored Rose Madder, Sheet 23.

*Stigmas.*—About 1/16 of an inch wide, plentiful. Collor—Aureolin, Sheet 3, No. 3/3.

*Ovaries.*—Plentiful.

Fruit: Usual form and abundance.

*Plant*

Form: A woody bush, generally upright, compact, symmetrical with flattened top.

Growth: About 2 feet to 2½ feet high at two years. Robust and very hardy.

Foliage: Open.

*Size.*—Length from 3 to 5 inches and width from 2 to 4 inches.

*Quantity.*—Medium.

*Color.*—New leaves, on top, Spinach Green, Sheet 187, No. 0960/1, with outer edges Indian Lake, Sheet 170, No. 826/3. Shiny on upper surface, dull on reverse. Old leaves Spinach Green, Sheet 187, No. 0960/1, on both surfaces.

*Shape.*—Normal, pinnate.

*Texture.*—Upper side smooth and glossy, lower face smooth and dull. Average thickness, borne alternately.

*Edge.*—Serrated.

Petiole: Length, about 2½ inches, smooth, strong. Color—Fern Green, Sheet 186, No. 0862/1 with midrib Indian Lake, Sheet 170, No. 826/3.

Stipules: Fern Green, Sheet 186, No. 0862/1.

Wood:

*Newest wood.*—Color—Spinach Green, Sheet 187, No. 0960/1.

*Old wood.*—Color—Spinach Green, same as new.

*Bark.*—Smooth.

Thorns:

*Quantity.*—Very few; on main stalks from base, few and on laterals, almost non-existent.

*Form.*—Short and stiff.

*Position.*—Evenly distributed on main stalks; on laterals and peduncles, almost non-existent.

The most distinctive feature and characteristic of the new hybrid tea-rose plant resides in the freedom of flowering, the size and shape of the flowers, the strength of the perfume, and the consistency of the color of the flowers and of the characteristics of the plant.

Having shown and described my new variety of hybrid tea-rose plant, and its manner of asexual reproduction, I claim:

The new and distince variety of hybrid tea-rose plant herein shown and described.

No references cited.